US008317718B2

(12) United States Patent
Bush et al.

(10) Patent No.: US 8,317,718 B2
(45) Date of Patent: Nov. 27, 2012

(54) METHODS OF TESTING DIGESTIVE FUNCTIONS USING BOTH A BREATH TEST AND A SCINTIGRAPHY TEST, AND METHODS OF USING A BREATH TEST AS AN OVERALL DIGESTIVE HEALTH ASSESSMENT

(75) Inventors: Kerry C. Bush, Brentwood, TN (US); Robert F. Martin, Missouri City, TX (US)

(73) Assignee: Advanced Breath Diagnostics, LLC, Brentwood, TN (US)

( * ) Notice: Subject to any disclaimer, the term of this patent is extended or adjusted under 35 U.S.C. 154(b) by 1239 days.

(21) Appl. No.: 12/116,418

(22) Filed: May 7, 2008

(65) Prior Publication Data

US 2008/0281194 A1 Nov. 13, 2008

Related U.S. Application Data

(60) Provisional application No. 61/016,023, filed on Dec. 21, 2007, provisional application No. 60/917,202, filed on May 10, 2007.

(51) Int. Cl.
*A61B 5/00* (2006.01)
*A61B 5/08* (2006.01)
*A61B 5/103* (2006.01)
*A61B 5/117* (2006.01)
*A61K 51/00* (2006.01)
*A61K 49/00* (2006.01)
*A61M 36/14* (2006.01)

(52) U.S. Cl. ........ 600/529; 600/300; 600/532; 600/593; 424/1.61; 424/1.73; 424/9.1

(58) Field of Classification Search .................... None
See application file for complete search history.

(56) References Cited

U.S. PATENT DOCUMENTS

| | | | |
|---|---|---|---|
| 4,985,232 A | | 1/1991 | Jacobssen |
| 5,707,602 A | | 1/1998 | Klein |
| 5,785,949 A | | 7/1998 | Klein |
| 6,432,382 B1 | | 8/2002 | Mehta |
| 6,548,043 B1 | | 4/2003 | Wagner |
| 6,740,305 B1 | | 5/2004 | Ajami |
| RE38,728 E | * | 4/2005 | Katzman et al. .............. 600/532 |
| 7,141,016 B2 | * | 11/2006 | Lykke et al. .................. 600/300 |
| 2003/0211042 A1 | * | 11/2003 | Evans et al. .................... 424/9.2 |
| 2004/0215068 A1 | * | 10/2004 | Lykke et al. .................. 600/302 |
| 2007/0014718 A1 | * | 1/2007 | Lee et al. ...................... 424/1.11 |
| 2008/0075658 A1 | * | 3/2008 | Burke et al. .................. 424/1.29 |
| 2008/0281166 A1 | * | 11/2008 | Bush et al. .................... 600/300 |
| 2008/0281194 A1 | * | 11/2008 | Bush et al. .................... 600/436 |
| 2008/0286200 A1 | * | 11/2008 | Bush et al. .................... 424/1.61 |
| 2011/0223104 A1 | * | 9/2011 | Bush et al. .................... 424/9.1 |

FOREIGN PATENT DOCUMENTS

| EP | 1503805 | * | 2/2005 |
|---|---|---|---|
| EP | 1624902 | * | 2/2006 |
| GB | 2360845 | | 10/2001 |
| WO | 97/35622 | | 10/1997 |
| WO | 01/72342 | | 10/2001 |
| WO | WO 2009/152222 A2 | * | 12/2009 |

OTHER PUBLICATIONS

Symonds et al, J. Nutr. 134: 1193-1196, 2004.*
Lee et al, Gut, 2000, 46:768-773.*
Bratten et al, Digestive Diseases, 2006, 24:252-259.*
Lin et al, Digestive Diseases and Sciences, Jun. 2005, 50/6:989-1004.*
Braden et al, Best Practice and Research Clinical Gastroenterology, 2009, 23:337-352.*
Szarka et al, Am. J. Physiol. Gastrointest. Liver Physiol., 2009, 296:G461-G475.*
Graham et al, American J. Gastroenterology, 2001, 96/6:1741-1745.*
Geypens et al, J. Nucl. Med., 1999, 40:1451-1455.*
Tougas et al, Am. J. Gastroenterology, 2000, 95/6:1456-1462.*
Ducrot et al, Digestive Diseases and Sciences, 1989, 34/5:657-664.*
Braden et al, Digestive and Liver Disease 39 (2007) 795-805.*
J S Lee, et al., "A Valid, Accurate, Office Based Non-Radioactive Test for Gastric Emptying of Solids" Gut 2000; 46:768-773.
B.E. Viramontes, et al., "Validation of a Stable Isotope Gastric Emptying Test for Normal, Accelerated or Delayed Gastric Emptying" Neurogastroenterol. Mot. (2001) 13, 567-574.
Yvo F. Ghoos, et al., "Measurement of Gastric Emptying Rate of Solids by Means of a Carbon-Labeled Octanoic Acid Breath Test" Gastroenterology 1993;104:1640-1647.
Abell et al., "Treatment of gastroparesis: a multidisciplinary clinical review", Neurogastroenterol Motil (2006) 18, 263-283.
B. Rosner, On the Detection of Many Outliers, Technometrics, 17/2, 221-227 (1975).
Breidthardt et al., "Medical and Economic Long-term Effects of B-type Natriuretic Peptide Testing in Patients with Acute Dyspnea", Clinical Chemistry 53:8 (2007), 1415-1422.
Bytzer et al., "GI Symptoms in Diabetes Mellitus are Associated with Both Poor Glycemic Control and Diabetic Complications" Am J Gastroenterology; 2002, vol. 97, No. 3, pp. 604-611.
Bytzer et al., "Prevalence of gastrointestinal symptoms associated with diabetes mellitus: a population-based survey of 15,000 adults," Arch Intern Med 2001; 161:1989-1996.
Chamorro et al., "Pharmacology and toxicology of spirulina alga," Rev Invest Clin Sep.-Oct. 1996; 48(5):389-99.
Chamorro et al., "Subchronic toxicity study in rats fed spirulina," J. Pharm Belg., 1988, 43, 1, 29-36.
Ciferri et al., "Spirulina the Edible Microorganism," Microbiological Reviews, Dec. 1983, p. 551-578.
Coste et al., "A Gray Zone Assigned to Inconclusive Results of Quantitative Diagnostic Tests: Application to the Use of Brain Natriuretic Peptide for Diagnosis of Heart Failure in Acute Dyspneic Patients", Clinical Chemistry 52:12 (2006), 2229-2235.
Enck et al., "Prevalence of gastrointestinal symptoms in diabetic patients and non-diabetic subjects," Z Gastroenterol 1994; 32:637-641.

(Continued)

*Primary Examiner* — Nita M Minnifield
(74) *Attorney, Agent, or Firm* — Fredrikson & Byron, P.A.

(57) ABSTRACT

Methods for assessing an overall digestive health of a patient are provided, which include administering a breath test that uses a label incorporated into proteins, carbohydrates, and lipids and further incorporating the labeled material into a meal which, when cooked, facilitates the binding of the label material to the solid phase matrix of the meal. Methods for assessing digestive functions of a patient are also provided, which includes concurrently administering a breath test and a scintigraphy test that measure gastric emptying in a stomach.

24 Claims, No Drawings

OTHER PUBLICATIONS

FDA Talk Paper, "Spirulina", Jun. 23, 1981.

Feinstein, "The inadequacy of binary models for the clinical reality of three-zone diagnostic decisions", J Clin Epidemiol, 43, 109-113 (1990).

Harris, et al., Statistical Bases of Reference Values in Laboratory Medicine, Marcel Dekker, 1995, Chapter 8: Analytical Goals for Reference Values.

Janatuinen et al., "Gastrointestinal symptoms in middle-aged diabetic patients," Scan J Gastroenterol 1993; 28:427-432.

Krishnakumari et al., "Food safety evaluation: acute oral and dermal effects of the algae scenedesmus acutus and spirulina platensis on albino rats", J. of Food Protection, vol. 44, No. 12, Dec. 1981, 934-935.

Lidums et al., "Effect of atropine on proximal gastric motor and sensory function in normal subjects", Gut 2000; 47:30-6.

Maleki et al., "Gastrointestinal tracts symptoms among persons with diabetes mellitus in the community," Arch Intern Med 2000; 160:2808-2816.

Park et al., "Clinical Reviews: Gastroparesis: Clinical Update" American Journal of Gastroenterology, ISSN 0002-9270 (2006), 1129-1139.

R.S. Chhikara et al, Extended critical Values of Extreme Studentized Deviate Test Statistics for Detecting Multiple Outliers, Commun. Statist.-Simula. Computa., B9(2), 155-166 (1980).

Salazar et al., "Effect of spirulina maxima consumption on reproduction and peri- and postnatal development in rats," Food and Chemical Toxicology, 34 (1996) 353-359.

Schofield, "Predicting basal metabolic rate, new standards and review of previous work", Hum Nutr Clin Nutr (1985) 39, 541.

Solberg, "RefVal: a program implementing the recommendations of the International Federation of Clinical Chemistry on the statistical treatment of reference values", Computer Methods and Programs in Biomedicine 1995, 48:247-256.

Szarda et al. "A Stable Isotope Breath Test with a Standard Meal for Abnormal Gastric Emptying of Solids in the Clinic and in Research", Clinical Gastroenterology and Hepatology, 2008; 6:635-643.

Talley et al., "Effects of a motilin receptor agonist (ABT-229) on upper gastrointestinal symptoms in type 1 diabetes mellitus: a randomized, double-blind, placebo controlled trial," Gut 2001; 49:395-401.

Talley et al., "Epidemiology of colonic symptoms and the irritable bowel syndrome," Gastroenterology 101:927-934, 1991.

Taub et al, "Irritable bowel syndrome defined by factor analysis. Gender and race comparisons." Dig Dis Sci 40:2647-2655, 1995.

Yoshino et al., "The chronic intoxication test of spirulina product fed to wistar rats," Japanese Journal of Nutrition, 38 (5), 1980, 221-226.

Zuckerman et al., "Healthcare-seeking behaviors related to bowel complaints. Hispanics versus non-Hispanic whites." Dig Dis Sci 41:77-82, 1996.

Bytzer et al., "Gastrointestinal symptoms in Diabetes Mellitus are Associated with Diabetic Complications but not with Current Glycemic Control," Abstract from Digestive Disease Week (DDW) 2000; Gastroenterology 2000; 118:A468.

* cited by examiner

METHODS OF TESTING DIGESTIVE FUNCTIONS USING BOTH A BREATH TEST AND A SCINTIGRAPHY TEST, AND METHODS OF USING A BREATH TEST AS AN OVERALL DIGESTIVE HEALTH ASSESSMENT

CROSS REFERENCE TO RELATED APPLICATIONS

This application claims priority to U.S. provisional patent application No. 61/016,023, filed Dec. 21, 2007, which in turn claims priority to U.S. provisional patent application No. 60/917,202, filed May 10, 2007, the entire contents of each of which are incorporated herein by reference.

BACKGROUND OF THE INVENTION

Processing of food begins in the oral cavity where food is mechanically broken down by mastication, lubricated with saliva, and enzymatically processed by amylase present in the saliva. Processing continues in the stomach where food is liquefied by gastric juices and enzymes secreted by the cells lining the stomach to produce chyme. Chyme enters the small intestine via the pyloric sphincter for further processing by bile salts produced by the liver and digestive enzymes produced by the pancreas. The small intestine absorbs most components from chyme through its walls, and the large intestine subsequently processes components that are not absorbed by the small intestine. Finally, the large intestine propels waste products into the colon, where they remain, usually for a day or two, until the feces are expelled by a bowel movement.

Typically, food includes proteins, carbohydrates, and fats. Each of these components passes through specific digestive and metabolic compartments. Proteins are first digested by enzymes in the juice of the stomach. Further digestion of the protein is completed in the small intestine. Here, several enzymes from the pancreatic juice and the lining of the intestine carry out the breakdown of huge protein molecules into amino acids. Amino acids can be absorbed from the hollow of the small intestine into the blood and then be carried to all parts of the body to build the walls and other parts of cells. Carbohydrates are broken into simpler molecules by enzymes in the saliva, in juice produced by the pancreas, and in the lining of the small intestine. For example, starch is digested in two steps. First, an enzyme in the saliva and pancreatic juice breaks the starch into molecules called maltose. Then, an enzyme in the lining of the small intestine (maltase) splits the maltose into glucose molecules that can be absorbed into the blood. Glucose is carried through the bloodstream to the liver, where it is stored or used to provide energy for the work of the body. Also, table sugar is digested by an enzyme in the lining of the small intestine, which converts it into glucose and fructose, each of which can be absorbed from the intestinal cavity into the blood. Milk contains yet another type of sugar, lactose, which is changed into absorbable molecules by an enzyme called lactase, also found in the intestinal lining.

Fat molecules are first dissolved in watery content of the intestinal cavity. Bile acids produced by the liver act as natural detergents to dissolve fat in water. Enzymes then break the large fat molecules into smaller molecules, some of which are fatty acids and cholesterol. The bile acids combine with the fatty acids and cholesterol and help these molecules to move into the cells of the mucosa. In these cells the small molecules are formed back into large molecules, most of which pass into vessels (called lymphatics) near the intestine. These small vessels carry the reformed fat to the veins of the chest, and the blood carries the fat to storage depots in different parts of the body.

Sometimes, a patient takes an abnormally long time to process and digest food, or a patient processes and digests food too quickly. This abnormal digestive behavior can be contributed to a disorder that affects the digestive system or the metabolic system, whether it is a disorder in the stomach or a disorder beyond the stomach. Commonly, a disorder occurs in the stomach that causes food to be emptied from the stomach into the small intestine too quickly or after too long of a time. Stomach emptying disorders can be diagnosed by measuring the rate at which a meal empties the stomach and enters the small intestine (the "gastric emptying rate"). When the rate is accelerated, undigested food is prematurely dumped from the stomach to the small intestine, giving rise to the condition termed "rapid emptying" or otherwise known as the dumping syndrome. Conversely, when the rate is decelerated, the movement of ingested food from the stomach to the small intestine is delayed, giving rise to the condition termed "delayed emptying" otherwise known as gastroparesis.

Two known tests for measuring gastric emptying rates are gastric scintigraphy tests and breath tests. In scintigraphy testing, a patient ingests a meal including at least one edible food, a component of which has been radiolabeled. The gamma emission from the radiolabel is measured by a scintillation camera as the labeled food is emptied from the stomach. Scintigraphy measurements of gastric emptying are direct, since the camera directly measures the amount of gamma emission from that portion of the radiolabeled meal retained in the stomach. In breath testing, a patient ingests a meal that includes a non-radioactive marker or label such as a stable isotope of carbon, carbon—13, denoted as $^{13}C$. As the non-radioactive labeled edible food is processed by the digestive tract and subsequent metabolic processes, a labeled component, such as $^{13}CO_2$, is produced which can be detected in the patient's breath. In contrast to scintigraphy, measurement of gastric emptying using breath testing is indirect. These two tests for measuring gastric emptying rates are limited to evaluating digestive disorders within only the stomach.

In other cases, a patient suffers from a disorder that occurs beyond the stomach. For example, the disorder can occur in the small intestine. In some cases, a patient might suffer from a shortage of the lactase enzyme in the small intestine, resulting in lactose intolerance. Tests for lactose intolerance include a hydrogen breath test. In this test a loading dose of approximately 2 grams of lactose in water per kilogram of body weight is administered to the patient. A baseline, pre-dose, breath sample is collected. After ingestion, additional breath samples are typically collected out to 3 hours. Hydrogen concentrations in excess of 20 parts per million compared to the baseline sample are considered indicative of lactose non-absorption. The abnormal amount of hydrogen is generated by bacterial fermentation of the lactose farther down the gut (colon) as a result of non-absorption in the small bowel. In other cases, a patient might suffer from a bacterial overgrowth in the small intestine, which can interfere with digestion and absorption of foods. Such a bacterial overgrowth can be detected by administering a $^{13}C$-xylose breath test to a patient. This test utilizes the simple 5-carbon carbohydrate xylose in which one or more of the carbon atom positions in the xylose molecule has had naturally occurring $^{12}C$ atoms replaced (or "labeled") with $^{13}C$ atoms. $^{13}C$-labeling in substrates like xylose may be achieved at isotopic purity levels exceeding 99%. The principle of this breath test is that the abnormal levels of small bowel flora can be detected by measuring the amount of $^{13}CO_2$ generated from bacterial $^{13}$C-xylose metabolism. Both the hydrogen breath test and the $^{13}$C-xylose breath test are limited to detecting disorders in the small intestine. In addition, these tests only measure activity related to the ingestion of a carbohydrate, and not proteins or fats.

In yet other cases, a patient might suffer from a metabolic disorder than occurs in an organ such as the pancreas or the liver. For example, a liver might not be functioning correctly, and liver functions can be assessed using a $^{13}$C-methionine breath test, a $^{13}$C-glucose breath test, or a $^{13}$C aminopyrine breath test. Again, these tests are limited to detecting disorders in the liver. In addition, in each of these tests, the $^{13}$C labeling of each respective compound may be achieved at levels exceeding 99% $^{13}$C isotopic purity.

Thus, while tests for measuring digestive or metabolic disorders are known, these tests are highly specific and use labels that are synthetically incorporated into a single specific molecule (substrate). For example, the $^{13}$C-xylose test uses a $^{13}$C label incorporated only into xylose, the $^{13}$C-methionine breath test uses a $^{13}$C label incorporated only into methionine, the $^{13}$C-glucose breath test uses a $^{13}$C label incorporated only into glucose, the $^{13}$C-aminopyrine breath test uses a $^{13}$C label incorporated into aminopyrine, and so on. As a result, these tests have been intended and limited to evaluating digestive or metabolic disorders within a single compartment and through a single metabolic pathway, for example only in the liver. As a result, if one of these tests yields a negative result (indicating that no disorder in the respective compartment is taking place), a clinician cannot assume that all of the patient's digestive and metabolic compartments are operating correctly. Instead, a clinician must perform additional tests at separate settings to evaluate additional compartments. It is also unfeasible to subject a patient to such additional testing, in order to obtain an overall digestive and metabolic assessment. Thus, it would be desirable to provide a simple test method for evaluating all of a patient's digestive and metabolic compartments. In addition, it would be desirable to provide a method for determining whether a digestive disorder occurs within the stomach or beyond the stomach.

SUMMARY OF THE INVENTION

In certain embodiments, a method of assessing an overall digestive health of a patient is provided. The method comprises administering a breath test that uses a label incorporated into proteins, carbohydrates, and lipids, obtaining a breath test result, and then designating the overall digestive health as healthy if the breath test result is normal or designating the overall digestive health as compromised if the breath test result is abnormal.

In other embodiments, a method of assessing digestive functions of a patient is provided, which includes concurrently administering a breath test and a scintigraphy test that measure gastric emptying in a stomach, wherein the breath test and the scintigraphy test are correlated to one another, obtaining a breath test result and a scintigraphy test result, and classifying the patient's digestive functions as normal, stomach abnormal, or post-stomach abnormal, wherein said normal classification is used when both the breath test result and the scintigraphy test result are normal, wherein said stomach abnormal classification is used when both the breath test result and the scintigraphy test result are abnormal, and wherein said post-stomach abnormal classification is used when the breath test result is abnormal and the scintigraphy test result is normal.

In other embodiments, a method of assessing digestive functions of a patient is provided, which includes administering a dual-label meal to a patient, the dual-label meal including a breath test label and a scintigraphic label, collecting a breath test sample and a scintigraphic scan concurrently at periodic time points, obtaining a scintigraphic test result and a breath test result for each of said periodic time points, providing an overall scintigraphic test result by evaluating the scintigraphic test result at each of said periodic time points, providing an overall breath test result by evaluating the breath test result at each of said periodic time points, and classifying the patient's digestive functions as normal, stomach abnormal, or post-stomach abnormal, wherein said normal classification is used when both the overall breath test result and the overall scintigraphy test result are normal, wherein said stomach abnormal classification is used when both the overall breath test result and the overall scintigraphy test result are abnormal, and wherein said post-stomach abnormal classification is used when the overall breath test result is abnormal and the overall scintigraphy test result is normal.

DETAILED DESCRIPTION OF THE INVENTION

The following detailed description depicts selected embodiments and are not intended to limit the scope of the invention. Skilled artisans will recognize that the examples given have many useful alternatives that fall within the scope of the invention.

A method is provided for assessing overall digestive health of a patient. The method includes administering a breath test that includes a label incorporated into proteins, carbohydrates, and lipids, and then obtaining a breath test result, the result being either a normal result or an abnormal result. The clinician simply designates the patient's overall digestive health as healthy if the breath test result is normal or compromised if the breath test result is abnormal.

The term "overall digestive health" is used herein to mean one of the following definitions: (1) the motility, digestive, absorptive, metabolic and excretory health of all or substantially all of the compartments that a breath test label must pass through before being expired in a patient's breath, (2) the motility, digestive, absorptive, metabolic and excretory health of the stomach, small intestine, liver, and lungs, or (3) the motility, digestive, absorptive, metabolic and excretory health of all or substantially all of the compartments that proteins, carbohydrates, and lipids must pass through in order to be digested, absorbed, and metabolized. The term "healthy" is used herein to mean freedom from digestive, absorptive, and/or metabolic disease or malfunctions in a compartment.

The method includes administering a breath test having a label that is incorporated into proteins, carbohydrates, and lipids. Applicant has discovered that using a breath test having a label incorporated into each of these food elements, and the labeled material being further incorporated and bound to a food matrix containing proteins, carbohydrates and lipids such as whole or rehydrated lyophilized eggs, can provide an overall assessment of a patient's digestive health, because these three elements are representative of the basic food categories and will be digested and metabolized in a manner that is consistent with normal food. In addition, since the label is incorporated into proteins, carbohydrates and lipids, the label is carried through all compartments that proteins, carbohydrates, and lipids must pass through during the course of normal processing, digestion, absorption and metabolism. As a result, the breath test measures multiple compartmental activities, including the digestion and gastric emptying properties of the stomach, further digestion and absorption across the small intestine mucosa, metabolism of absorbed nutrients by the liver, and the excretion of the breath test label via transport in the bicarbonate pool, and excretion in the lungs. This includes far more digestive, absorptive and metabolic pathways than labels in prior breath tests pass through, because prior tests include labels that are only incorporated into a single molecular element of food, such as only in glucose (a simple carbohydrate) or only in leucine (an amino acid). Skilled artisans previously only viewed breath test results as indicative of whether any single compartment, when specifically targeted with a specifically labeled molecule, is compromised.

This method of using a breath test to assess a patient's overall digestive health is advantageous because it can be used on a widespread basis, such as in a hospital setting, in an outpatient or clinic setting or in a point of care settings. For example, breath tests can easily be administered during routine physicals to routinely screen patients for digestive disorders.

In certain cases, the breath test uses a $^{13}C$ label that is incorporated into biomass. Biomass, such as algal biomass, is composed of cells that include carbohydrate, protein, and lipids. In specific cases, the breath test uses a $^{13}C$ label incorporated into *Spirulina platensis*. *Spirulina platensis* labeled with $^{13}C$ can be obtained by growing the algal cells in a $^{13}C$-enriched environment as is disclosed in commonly assigned U.S. Pat. No. 6,872,516, the disclosure of which is herein incorporated by reference in its entirety. *Spirulina platensis* was acknowledged by the US Food and Drug Administration as a legally marketed food in 1981 and is currently consumed in the US as a dietary supplement in recommended amounts of 3-4.5 grams daily. *Spirulina platensis* can be uniformly labeled with $^{13}C$ to an abundance level of approximately 99% and contains approximately 50-60% proteins, 30% carbohydrates and 10% lipids.

The $^{13}C$-*Spirulina platensis* can be ingested by a patient at a dose of 200 mg or less to provide an excellent signal in breath testing. In certain cases, the dose is approximately 100 mg, which contains approximately 43 mg of $^{13}C$. In some cases, the $^{13}C$-*Spirulina platensis* is further provided as part of a meal. The meal can include any food type suitable for human consumption. The term "meal" is referred to herein as any number of edible food components ingested at a single setting. A single setting can be a designated time period, perhaps a period of less than 30 minutes, 20 minutes, or even 10 minutes. In many cases, a meal can include a main food component as well as any sides and liquids. In certain cases, the meal includes components derived from standardized, freeze-dried or lyophilized components. Suitable freeze-dried components are described in U.S. patent application Ser. No. 10/435,092, the entire contents of which are incorporated herein by reference.

In one embodiment, the meal includes components derived from lyophilized eggs. In one particular embodiment, the meal includes whole eggs and $^{13}C$-*Spirulina platensis* that has been lyophilized together and then reconstituted. In certain embodiments, the meal includes eggs, bread, and milk, or eggs, crackers and water. In particular cases, the meal includes two scrambled eggs, a slice of wheat toast, and 8 ounces of skim milk.

One exemplary method of assessing a patient's overall digestive health will now be described. A patient preferably fasts for a period of time, for example at least about eight hours, before the test is administered. This may be conveniently done by asking the patient to refrain from eating after midnight and then administering the test meal as breakfast. In addition, the patient preferably refrains from drinking more than about four fluid ounces of water up to one hour before the test. Baseline breath samples are collected, such as by blowing into a screw-cap test tube with a straw or into a breath bag with mouth piece with an appropriate one-way valve before the meal is administered to determine the pre-meal baseline ratio of $^{13}CO_2/^{12}CO_2$ in the breath.

A patient is then given a meal that includes a label that is incorporated into proteins, carbohydrates, and lipids. In certain cases, the meal includes $^{13}C$-*Spirulina platensis*. The patient also consumes the meal in a single setting, for example within a 10 minute time frame. After the meal is consumed, the breath testing procedure is performed. For example, breath samples can be obtained after the meal is consumed at periodic time points, such as at 45, 90, 120, 150, 180, and 240 minute time points.

In some cases, breath samples are collected in glass tubes using a straw to blow into the bottom of the tube to displace contained air and capture a clean breath sample. Alternatively, they may be captured by utilizing a breath bag. The tubes are capped and the $^{13}CO_2$ content of the breath for each tube (and thus for each time point) may be determined using Gas Isotope Ratio Mass Spectrometry or Infrared Spectroscopy. These measurements may be performed, for example, using instruments approved by the FDA for measurement of $^{13}CO_2/^{12}CO_2$ ratios in human breath. For example, the measurements may be made by mass spectrometers, such as those manufactured by Europa Instruments of the United Kingdom, or using infrared spectrometers, such as those available from Otsuka Electronics Co., Ltd.

The $^{13}CO_2/^{12}CO_2$ ratios are then used to calculate the $^{13}CO_2$ excretion rate at each respective timepoint. The measured $^{13}CO_2/^{12}CO_2$ ratios and/or the calculated $^{13}CO_2$ excretion rate at one or more time points can then be classified as normal or abnormal, using known classification methods in the art. If the results are normal, the patient's overall digestive health is designated as healthy. Normal results will typically be consistent with the range of breath test results found in healthy individuals with no known disease or malfunctions in any compartments.

In some embodiments, a breath test is considered normal at a given time point if it falls within the reference range illustrated in Table 1, as further described below. Table 1 shows the normal reference ranges for a 45 minute, 90 minute, 120 minute, 150 minute, and 180 minute time point. These ranges have been calculated for a 225 kcal meal that includes potable water, six Nabisco PREMIUM crackers, and lyophilized whole eggs bound to $^{13}C$-*Spirulina platensis* at a dosage of about 100 mg.

In some cases, the breath test measurements are determined to be normal or abnormal at a series of time points, the series of time points including a 45 minute time point, a 90 minute time point, a 120 minute time point, a 150 minute time point, and a 180 minute time point. The selecting of a normal or an abnormal classification includes (1) selecting a normal result if the breath test measurement is between a 12.9 and 32.9 kPCD range or selecting abnormal result if the breath test is outside this range at the 45 minute time point, (2) selecting a normal result if the breath test measurement is between a 33.1 and 63.2 kPCD range or selecting abnormal result if the breath test is outside this range at the 90 minute time point, (3) selecting a normal result if the breath test measurement is between a 44.2 and 72.5 kPCD range or selecting abnormal result if the breath test is outside this range at the 120 minute time point, (4) selecting a normal result if the breath test measurement is between a 49.3 and 74.5 kPCD range or selecting abnormal result if the breath test is outside this range at the 150 minute time point, and (5) selecting a normal result if the breath test measurement is between a 46.5 and 70.5 kPCD range or selecting abnormal result if the breath test is outside this range at the 180 minute time point. The overall breath test result can be designated as normal or abnormal by observing one or more measurements in the series of time points.

Although the normal range has been determined at multiple time points during digestion of the meal, all time points are informative but not necessary to assess nutritional health. A substantial $^{13}C$ signal can be observed as early as 45 minutes after consuming the meal, meaning that digestion, absorption, and metabolism of the $^{13}C$-labeled substrate, e.g. biomass, (and the meal to which it is bound) are all occurring actively. Because this meal empties in about 3 hours in healthy individuals, a 90 minute, 120 minute or 150 minute time point may used because a substantial proportion of the meal has been digested and all compartments have been actively engaged. For example, at 120 minutes, patients having kPCD values between 44.2 and 72.5 would be classified as having normal digestive health. Those having kPCD values < or > the normal range limits would be considered to have compromised digestive health. Subsequent follow-up to determine if the problem is stomach or post stomach may be pursued as previously described.

If the breath test result is abnormal, the clinician is unable to give the patient a healthy diagnosis and instead designates the patient's overall digestive health as compromised. The clinician then performs additional tests to locate which compartment the disorder occurs in, and also determines the cause of the disorder. Once the disorder is determined, the clinician can administer a treatment. After treatment, an additional breath test can be performed to obtain a post-treatment result. A clinician can then compare the post-treatment result with the original result, to determine whether the disorder is improving. In such cases, the same breath test is first used as an overall digestive health test and then is used to monitor treatment results.

Methods for determining whether a digestive disorder occurs in the stomach or beyond the stomach are also provided. Such methods can involve concurrently administering both a breath test and a gastric scintigraphy test. In certain embodiments, the breath test is of the type already described, which uses a label that is incorporated into proteins, carbohydrates, and lipids. Applicant has discovered that when both a breath test and a gastric scintigraphy test, which have a diagnostic concordance with each other in regards to measurements of gastric emptying, are performed on a patient concurrently, sometimes the breath test yields an abnormal result whereas the scintigraphy test yields a normal result. These differences were unexpected because both tests where being used to assess the same thing—the gastric emptying rate.

Applicant has subsequently discovered that certain patients having contradicting tests results did not have a stomach disorder affecting gastric emptying but did have another digestive disorder beyond the stomach. As a result, the scintigraphy test did not detect abnormal activity within the stomach (that is, the stomach emptied normally) but the breath test did detect abnormal activity beyond the stomach. Thus, Applicant has discovered that breath tests, which were intended to be utilized solely for measuring the rate of gastric emptying, are capable of indicating digestive disorders occurring in compartments beyond the stomach, such as in the small intestine or liver.

In certain embodiments, a method for determining whether a digestive disorder occurs within the stomach or beyond the stomach is provided. A clinician concurrently administers a breath test and a gastric scintigraphy test to a patient. The breath test and scintigraphy test preferably have a diagnostic concordance with each other. That is, the breath test can be used as a surrogate test to scintigraphy, and vice-versa. A clinician then obtains the results from each test and uses the results to determine whether a patient has a digestive disorder within the stomach and/or beyond the stomach. Generally, a clinician obtains either a negative (normal) or positive (abnormal) result from each test, and then makes the following deductions:

I. A negative (normal) result by both methods tells the clinician that both the stomach and post-stomach process are normal and intact. The patient's digestive functions are characterized as "normal".

II. A positive (abnormal) result by both methods indicates that the stomach is operating abnormally, that is, either too slow or too fast. In cases where the gastric emptying rate is in concurrence by both methods, that is both methods indicate the patient is outside the established normal range of gastric emptying rates (fast or slow), this confirms the problem is likely to be limited to the stomach. The patient's digestive functions are characterized as "stomach abnormal".

III. A negative (normal) result by scintigraphy with a positive (abnormal) result by the breath test informs the clinician that the stomach is operating normally but there is a post-stomach problem that may require further investigation to explain the patient's symptoms or problems. The patient's digestive functions are characterized as "post-stomach abnormal".

Thus, a patient's digestive functions are classified as normal, stomach-abnormal, or post-stomach abnormal. In some cases, discrimination of a potential problem both in and beyond the stomach can be discerned when the results of the 2 tests are the same (both are abnormal) but the severity is different. For example, both the scintigraphy test and breath test may yield an abnormal gastric emptying result, e.g. slow, but the breath test may show a significantly more severe slow result. Applicant has discovered that valuable information can be obtained from the results of concurrently administered breath and gastric scintigraphic tests. In addition, Applicant has discovered that a normal result obtained by a breath test indicates that all digestive processes in the stomach and beyond the stomach are operating well, as already discussed above.

The breath test and scintigraphy test can each be tests known in the art. In some cases, the breath test is administered by supplying the patient with a meal containing a $^{13}C$ label. The $^{13}C$ label is incorporated into a substrate or source that is suitable for human consumption. For example, the source can be octanoic acid or an algae such as *Spirulina platensis*, as already discussed above. In certain embodiments, the breath test is administered in accordance with the methods already described above and the source includes proteins, carbohydrates, and lipids. A clinician obtains $^{13}CO_2/^{12}CO_2$ ratios and calculates the change in $^{13}CO_2$ excretion over time, which can then be used to determine the rate of gastric emptying, in accordance with calculation methods known in the art.

Further, in some cases, the scintigraphic test can be administered by supplying the patient with a meal containing a scintigraphic label. The scintigraphic label can be any such label known in the art, such as $^{99m}Tc$ (technetium). In some cases, $^{99m}Tc$ sulphur colloid is provided in the meal at a dose of about 0.5 mCi. A gamma emission camera is positioned over the patient's abdomen as the meal and scintigraphic label bound to the meal moves out of the stomach. The camera takes scans of the gamma emission from the scintigraphic label at different time points and the % of the meal emptied at each time point is determined. The rate of gastric emptying is determined from these percentages, in accordance with calculation methods known in the art. Once the rate of gastric emptying for each method is determined, it is classified as normal or abnormal. A clinician then uses the normal or abnormal result obtained for each method to make the deductions described above.

In some cases, the scintigraphy test and the breath test are administered independently utilizing the same meal by having a patient ingest two separate meals on separate occasions, with one meal having a $^{13}C$ label and the other meal having a scintigraphic label. In other cases, both the breath test and the scintigraphic test are administered by supplying the patient with a single meal that contains both a $^{13}C$ label and a scintigraphic label. Such a meal is referred to herein as a dual-label meal. The $^{13}C$ label can be of the types already described and the scintigraphic label can include any radiolabel known in the art, such as $^{99m}Tc$ sulphur colloid.

The dual-label meal can include any food type suitable for human consumption, as already described above. In certain embodiments, the dual-label meal has an edible food component labeled with both a radiolabel, such as $^{99m}Tc$ sulphur colloid, and a $^{13}C$-label, such as $^{13}C$-*Spirulina platensis*. In certain cases, the meal includes 0.5 mCi $^{99m}Tc$ sulphur colloid and 100 mg of $^{13}C$-*Spirulina platensis*. One exemplary meal will now be described. A lyophilized powder containing both a pasteurized scrambled egg mix and approximately 100 mg of $^{13}C$-*Spirulina platensis* is rehydrated with potable water. Approximately 0.5 mCi $^{99m}Tc$ sulphur colloid is added to the rehydrated egg mix to provide an egg mix including both about 100 mg of $^{13}C$-*Spirulina platensis* and about 0.5 mCi of $^{99m}Tc$ sulphur colloid. The egg mix is then cooked, for example in a microwave. A patient can be given the cooked egg mix along with other optional edible food components, such as six Nabisco PREMIUM Saltine crackers and six ounces of potable water. The entire meal is preferably around 225 kCal and takes a normal patient about three hours to empty from the stomach.

One exemplary method of concurrently administering both a breath test and a scintigraphic test will now be described. A patient preferably fasts for a period of time, for example at least about eight hours, before the tests are administered. In addition, the patient preferably refrains from drinking more than about four fluid ounces of water up to one hour before the test. Baseline breath samples are collected before the meal is administered to determine the pre-meal baseline ratio of $^{13}CO_2/^{12}CO_2$ in the breath. A patient is then given a dual-labeled meal. In certain cases, the dual-labeled meal includes $^{13}C$-*Spirulina platensis* and $^{99m}Tc$ sulphur colloid. The patient also consumes the meal in a single setting, preferably within a 30 minute time frame, such as a 10 minute time frame.

After the meal is consumed, both the scintigraphic and breath testing procedures are simultaneously performed. Scintigraphic scans and breath samples are obtained after the meal is consumed at periodic time points. In certain cases, the periodic time points include 45, 90, 120, 150, 180, and 240 minute time points. One or more gamma emission cameras are positioned about the patient's abdomen in order to record the movement of the meal and scintigraphic label out of the stomach. The cameras take a scan and record the gamma emission from the scintigraphic label at each time point. Breath samples are also collected at each time point and the $^{13}CO_2$ content of the breath is determined, for example by using Gas Isotope Ratio Mass Spectrometry or Infrared Spectroscopy, as already discussed above.

Applicant has also developed two metrics in common that can be used to express breath test results: kPCD and CumPCD. The PCD metric is the Percent Dose (abbreviated PCD) of $^{13}C$ excreted at time t after consumption of the test meal. Since the original $^{13}C$ dose administered is known, e.g. 43 mg of $^{13}C$ contained in 100 mg of $^{13}C$-labeled *Spirulina*, one can calculate the percent $^{13}C$ dose excreted by the patient by analyzing the $^{13}CO_2$ content in the breath specimens as will be further described below. To provide a more convenient scale, PCD is multiplied by 1000 to produce kPCD at any time, t. CumPCD is the cumulative dose of $^{13}C$ excreted at time t. The kPCD and CumPCD can be determined for each time point t after consumption of the test meal, usually at 45, 90, 120, 150, 180, and 240 minute time points. For each time t, the kPCD can be calculated as follows:

$$kPCD_t = \left[\frac{DOB * CO_2PR * R_s * 13}{10 * \text{dose}}\right] * 1000$$

where:
DOB=The measured difference in the $^{13}CO_2/^{12}CO_2$ ratio between a post-meal breath specimen at any time t and the baseline breath specimen.
$CO_2PR=CO_2$ production rate (mmol $CO_2$/min) calculated using the Scholfield equations. The Scholfield equations are a set of equations which are fitted to people depending on their age, gender, height, and weight to estimate the basal metabolic rate (BMR), which is intimately related to $^{13}CO_2$ production rate. The equations allow the calculation of a specific $CO_2$ production rate for the individual being tested.
$R_s$=0.0112372, the ratio [$^{13}CO_2/^{12}CO_2$] in an international reference standard (Pee Dee belemite-PDB).
13=The atomic weight of $^{13}C$.
10=A constant factor for converting units.
Dose=The weight (mg) of $^{13}C$ in the dose of $^{13}C$-*Spirulina platensis* administered to the patient in the test meal. For example, since $^{13}C$-*Spirulina platensis* is approximately 43% $^{13}C$, a dose of 100 mg corresponds to approximately 43 mg of $^{13}C$.

The kPCD is calculated for each time point t, which in most cases includes 45, 90, 120, 150, 180, and 240 time points. Applicant also calculates CumPCD, which is the calculation of the area under the PCD curve and is accomplished by trapezoidal integration:

$$CUMPCD_n = \sum_{i=1}^{i=n} \frac{(PCD_i + PCD_{i-1})(t_i - t_{i-1})}{2}$$

where $PCD_i$ and $t_i$ represent the PCD value (in μmol/min) and time (in minutes) at the $i^{th}$ breath collection time point.

Furthermore, scintigraphic test results can be expressed as $Prop_t$, which is the proportion of a radioactive label emptied from the stomach at a given time t. $Prop_t$ may be expressed at "% meal emptied," or as "% emptied," or "% Prop." In scintigraphic testing, a region of interest is drawn around the stomach on the anterior and posterior images for each time point. To correct for attenuation, the counts of each are multiplied together and the square root of the product is taken to obtain the geometric mean.

The breath test and the scintigraphic test measurements for each time point are then analyzed to determine whether a normal or abnormal result is obtained by each respective method. The measurements can be classified as normal or abnormal using any analyzing means known in the art. In certain cases, the measurements are compared to a reference range for each time point prospectively established for each method. An exemplary set of reference ranges for a specifically formulated egg meal are illustrated in Table 1 below. The specifically formulated egg meal is a 225 kCal meal that includes potable water, six Nabisco PREMIUM crackers, and lyophilized whole eggs. For the breath test, the whole eggs were bound to $^{13}C$-*Spirulina platensis* at a dosage of about 100 mg. For the scintigraphy test, the whole eggs were bound to $^{99m}Tc$ sulphur colloid at a dosage of about 0.5 mCi. The egg meal takes a normal patient about 3 hours (180 minutes) to empty from the stomach.

TABLE 1

95% Central Reference Ranges for the
Gastric Emptying Breath Test and Scintigraphy

| Measurement Time (minutes) | Breath Test Reference Range (kPCD) | Breath Test Reference Range (CumPCD) | Scintigraphy Reference Range (% Prop) |
|---|---|---|---|
| 45 | 12.9-32.9 | 0.291-0.744 | 18.1-50.5 |
| 90 | 33.1-63.2 | 1.223-2.880 | 49.4-80.9 |
| 120 | 44.2-72.5 | 2.153-4.872 | 67.8-95.1 |
| 150 | 49.3-74.5 | 4.001-7.041 | 77.4-100 |
| 180 | 46.5-70.5 | 5.529-9.143 | 87.5-100 |

The reference ranges in Table 1 were calculated using both breath test and scintigraphic test results from normal healthy subjects. Specifically, reference ranges for kPCD and CumPCD for the breath test and Prop (proportion of meal emptied) for scintigraphy for normal test subjects were calculated at each measured time point using RefVal, a program implementing the recommendations of the International Federation of Clinical Chemistry on the statistical treatment of reference values. Though several statistical procedures are implemented in RefVal, Applicant focused on the parametric estimation method based on a two-stage mathematical transformation of data: (1) Manly's exponential transformation—to remove skewness and (2) John and Draper's modulus transformation—to adjust for residual kurtosis. Either the kPCD or the CumPCD ranges can be observed for the breath test. Preferably, the kPCD ranges will be observed.

Once the 95% central reference ("normal") ranges for each time point were calculated, the upper and lower cutoff points of the normal range of gastric emptying values were set. Essentially, the RefVal calculations take all the values derived from the healthy subjects and then cuts out the bottom 2.5% of the values and the upper 2.5% of the values, leaving the remaining 95% of the values as the normal range. Hence, the lower 2.5% fractile bound of the central 95% reference range is the lower cutoff point and demarcates normal from slow emptying. Likewise, the upper 2.5% fractile bound of the central 95% reference range is the upper cutoff point and demarcates normal from rapid emptying. In Table 1, the lower cutoff point for either method at a given time point is the lower limit of the normal range. Likewise, the upper cutoff point is the upper limit of the normal range. For example, using the values in Table 1, at 120 minutes, the lower kPCD cutoff point is 44.2 and the upper kPCD cutoff point is 72.5.

These 95% central reference ranges (the "normal ranges") are useful for making a variety of clinical observations. If the measurement obtained for a particular time point falls within the given normal range (the kPCD range for breath test measurements and the Prop range for scintigraphy test measurements), the result for that time point is normal. Likewise, if the measurement obtained falls below the normal range cutoff value, the result for that time period is positive for delayed emptying and is thus abnormal. If the measurement falls above the normal range cutoff value, the result is positive for rapid emptying and is thus abnormal. For example, at the 120 minute time point, kPCD measurements that fall below 44.2 are considered positive for delayed emptying and are abnormal. The lower the number, the more severe the delay, with a value of zero representing a completely nonfunctional stomach. kPCD measurements that fall above 72.5 are considered positive for rapid emptying and are abnormal. kPCD measurements that fall within the 44.2-72.5 range are considered normal. Likewise, $Prop_t$ measurements that fall below 67.8 are considered positive for delayed emptying and are abnormal. Again, the lower the number, the greater the delay, with a value of zero representing a completely non-functional stomach. $Prop_t$ measurements that fall above 95.1 are considered positive for rapid emptying and are abnormal.

Thus, in some embodiments, for each time point, a scintigraphic reference range and a breath test reference range is established. Each of the respective scintigraphic and breath test reference ranges reflects a range of test results observed in normal patients. If the scintigraphic test measurement falls within the scintigraphic 95% central reference range, the scintigraphic test result for that time point is normal, whereas if the measurement falls outside the range, the test result is abnormal. Likewise, if the breath test measurement falls within the breath test 95% central reference range, the breath test result for that time point is normal, whereas if the measurement falls outside the range, the test result is abnormal.

Once the scintigraphic test result and the breath test result has been obtained for each time point (e.g., 45 minutes, 90 minutes, 120 minutes, 150 minutes, and 180 minutes), a clinician can evaluate the overall test.

In some cases, the breath test measurements are determined to be normal or abnormal at each of these time points. The selecting of normal or abnormal includes (1) selecting a normal result if the breath test measurement is between a 12.9 and 32.9 kPCD range or selecting abnormal result if the breath test is outside this range at the 45 minute time point, (2) selecting a normal result if the breath test measurement is between a 33.1 and 63.2 kPCD range or selecting abnormal result if the breath test is outside this range at the 90 minute time point, (3) selecting a normal result if the breath test measurement is between a 44.2 and 72.5 kPCD range or selecting abnormal result if the breath test is outside this range at the 120 minute time point, (4) selecting a normal result if the breath test measurement is between a 49.3 and 74.5 kPCD range or selecting abnormal result if the breath test is outside this range at the 150 minute time point, and (5) selecting a normal result if the breath test measurement is between a 46.5 and 70.5 kPCD range or selecting abnormal result if the breath test is outside this range at the 180 minute time point. The overall breath test result can be designated as normal or abnormal by observing one or more measurements in these time points.

Likewise, the scintigraphy test measurements are determined to be normal or abnormal at each of these time points. The selecting of normal or abnormal includes (1) selecting a normal result if the scintigraphy test measurement is between a 18.1 and 50.5% Prop range or selecting abnormal result if the scintigraphy test is outside this range at the 45 minute time point, (2) selecting a normal result if the scintigraphy test measurement is between a 49.4 and 80.9% Prop range or selecting abnormal result if the scintigraphy test is outside this range at the 90 minute time point, (3) selecting a normal result if the scintigraphy test measurement is between a 67.8 and 95.1% Prop range or selecting abnormal result if the scintigraphy test is outside this range at the 120 minute time point, (4) selecting a normal result if the scintigraphy test measurement is between a 77.4 and 100% Prop range or selecting abnormal result if the scintigraphy test is outside this range at the 150 minute time point, and (5) selecting a normal result if the scintigraphy test measurement is between a 87.5 and 100% Prop range or selecting abnormal result if the scintigraphy test is outside this range at the 180 minute time point. The overall scintigraphy test result can be designated as normal or abnormal by observing one or more measurements in these time points.

In some cases, if one of the time points yields an abnormal result, the overall test result is considered abnormal. In certain cases, a clinician observes only one or two of the time points to determine an overall test result. In certain embodiments, a clinician observes a first time point and a second time point, wherein if either the first time point or second time point yields an abnormal result, the overall test result is considered abnormal. For example, in certain embodiments, the first time point is a 120 minute (2 hour) time point and the second time point is a 240 (4 hour) time point. In other cases, the first time point is a 90 minute (1½ hour) time point and the second time point is a 180 (3 hour) time point. Generally, the time points observed can depend on how fast the standardized meal is expected to be emptied in a normal patient. For example, if the meal is expected to be emptied in 3 hours, the 90 minute (1½ hour) and 180 minute (3 hour) time points may be used. Likewise, if the meal is expected to be emptied in 4 hours, the 120 minute (2 hour) and/or 240 minute (4 hour) time points are used. In other embodiments, only one time point, e.g., the 90 minute or 120 minute time point can be used. If one gives both labels in one meal and conducts both test as described herein, then results in which the scintigraphic result is normal but breath test is slow, should lead the clinician to suspect digestive or metabolic issues beyond the stomach.

The reference ranges illustrated in Table 1 can be adjusted and changed, such as when new meals of different compositions are developed. Skilled artisans will understand how the reference ranges are obtained and can recreate them with new data. In addition, other mechanisms for classifying measurements for breath test and scintigraphic tests can be used, in order to provide a normal or abnormal result. The normal or abnormal results can then be used to determine whether a patient has digestive problems in the stomach or beyond the stomach, as described above.

In some cases, results of the breath test depend upon the operation of the stomach, small intestine absorption, liver metabolism and lung function and other related processes (e.g. pancreas). Here, the clinician can begin with these compartments as the cause for the abnormal results and can begin to assess the patient accordingly. For example, if the patient has normal scintigraphic gastric emptying test but a breath test result which is slow (below the lower limit of the normal range), the clinician may pursue, via patient history and clinical tests, clinical problems that affect pancreatic function, small bowel function (such as celiac disease), liver impairment (such as cirrhosis, infection, or malignancy), or even lung dysfunction (such as chronic obstructive pulmonary disease).

It should be further noted that if and when a post compartment disorder is found, the breath test can be utilized alone to assess and/or monitor the patient's status and or response to therapy. For example, celiac disease is a condition that affects the mucosa of the small intestine and interferes with the normal absorption of nutrients. If unrecognized and untreated, celiac disease can result in up to 20% mortality and significantly increases the risk for intestinal neoplasms. Treatment, which includes a gluten free diet, usually improves the status of the patient. The breath test could have significant utility in managing the patient's status in response to therapy and dietary changes. This is but one example, but many additional conditions, once identified, that affect post stomach compartments, could be monitored via a digestive health breath test.

What is claimed is:

1. A method of assessing digestive functions of a patient, wherein the digestive functions include digestive functions that occur post-stomach, the method comprising:
    concurrently administering a breath test and a scintigraphy test that measure gastric emptying in a stomach, wherein the breath test and the scintigraphy test have a diagnostic concordance to one another, wherein the breath test uses a label incorporated into proteins, carbohydrates, and lipids;
    obtaining a breath test result, the breath test result being either normal or abnormal;
    obtaining a scintigraphy test result, the scintigraphy test result being either normal or abnormal; and
    classifying the patient's digestive functions as normal, stomach abnormal, or post-stomach abnormal, wherein said normal classification is used when both the breath test result and the scintigraphy test result are normal, wherein said stomach abnormal classification is used when both the breath test result and the scintigraphy test result are abnormal, and wherein said post-stomach abnormal classification is used when the breath test result is abnormal and the scintigraphy test result is normal.

2. The method of claim 1, wherein the classifying the patient's digestive function further comprises classifying the patient's digestive function as both stomach abnormal and post-stomach abnormal when the breath test result and scintigraphy test result are each abnormal and the breath test data is inconsistent with the scintigraphy test data.

3. The method of claim 1, wherein the classifying the patient's digestive function as stomach abnormal comprises classifying the digestive function as stomach abnormal only when the breath test data is consistent with the scintigraphy test data.

4. The method of claim 1, wherein the obtaining a breath test result comprises selecting a normal time point result or an abnormal time point result at a series of time points, the series of time points including a 45 minute time point, a 90 minute time point, a 120 minute time point, a 150 minute time point, and a 180 minute time point, the selecting including:
    selecting a normal time point result if the breath test yields a measurement that is between a 12.9 and 32.9 kPCD range or selecting an abnormal time point result if the breath test is outside of the 12.9 and 32.9 kPCD range at the 45 minute time point;
    selecting a normal time point result if the breath test yields a measurement that is between a 33.1 and 63.2 kPCD range or selecting an abnormal time point result if the breath test is outside of the 33.1 and 63.2 kPCD range at the 90 minute time point;
    selecting a normal time point result if the breath test yields a measurement that is between a 44.2 and 72.5 kPCD range or selecting an abnormal time point result if the breath test is outside of the 44.2 and 72.5 kPCD range at the 120 minute time point;
    selecting a normal time point result if the breath test yields a measurement that is between a 49.3 and 74.5 kPCD range or selecting an abnormal time point result if the breath test is outside of the 49.3 and 74.5 kPCD range at the 150 minute time point; and
    selecting a normal time point result if the breath test yields a measurement that is between a 46.5 and 70.5 kPCD range or selecting an abnormal time point result if the breath test is outside of the 46.5 and 70.5 kPCD range at the 180 minute time point, wherein the breath test result is designated as normal or abnormal by observing one or more measurements in the series of time points.

5. The method of claim 1, wherein the obtaining a scintigraphy test result comprises selecting a normal time point result or an abnormal time point result at a series of time points, the series of time points including a 45 minute time point, a 90 minute time point, a 120 minute time point, a 150 minute time point, and a 180 minute time point, the selecting including:
  selecting a normal time point result if the scintigraphy test yields a measurement that is between a 18.1 and 50.5% Prop range or selecting an abnormal time point result if the scintigraphy test is outside of the 18.1 and 50.5% Prop range at the 45 minute time point;
  selecting a normal time point result if the scintigraphy test yields a measurement that is between a 49.4 and 80.9% Prop range or selecting an abnormal time point result if the scintigraphy test is outside of the 49.4 and 80.9% Prop range at the 90 minute time point;
  selecting a normal time point result if the scintigraphy test yields a measurement that is between a 67.8 and 95.1% Prop range or selecting an abnormal time point result if the scintigraphy test is outside of the 67.8 and 95.1% Prop range at the 120 minute time point;
  selecting a normal time point result if the scintigraphy test yields a measurement that is between a 77.4 and 100% Prop range or selecting an abnormal time point result if the scintigraphy test is outside of the 77.4 and 100% Prop range at the 150 minute time point; and
  selecting a normal time point result if the scintigraphy test yields a measurement that is between a 87.5 and 100% Prop range or selecting an abnormal time point result if the scintigraphy test is outside of the 87.5 and 100% Prop range at the 180 minute time point, wherein the scintigraphy test result is designated as normal or abnormal by observing one or more measurements in the series of time points.

6. The method of claim 1, wherein said label is incorporated into a biomass composed of cells including proteins, carbohydrates, and lipids.

7. The method of claim 6, wherein said biomass is *Spirulina platensis*.

8. The method of claim 1 wherein said breath test label is $^{13}C$.

9. The method of claim 1, wherein the concurrently administering a breath test and a scintigraphy test comprises administering to a patient a single meal containing both a breath test label and a scintigraphic label.

10. The method of claim 9, wherein the single meal is ingested within a period of time of less than about 30 minutes.

11. The method of claim 9, wherein the single meal includes $^{13}C$-*Spirulina platensis* in an amount of about 100 mg and $^{99m}Tc$ sulphur colloid in an amount of about 0.5 mCi.

12. A method of assessing digestive functions of a patient, wherein the digestive functions include digestive functions that occur post-stomach, the method comprising:
  administering a dual-label meal to a patient, the dual-label meal including a breath test label and a scintigraphic label, wherein the breath test label is incorporated into proteins, carbohydrates, and lipids;
  collecting a breath test sample and a scintigraphic scan at periodic time points;
  obtaining a scintigraphic test result and a breath test result for each of said periodic time points;
  providing an overall scintigraphic test result by evaluating the scintigraphic test result at each of said periodic time points;
  providing an overall breath test result by evaluating the breath test result at each of said periodic time points; and
  classifying the patient's digestive functions as normal, stomach abnormal, or post-stomach abnormal, wherein said normal classification is used when both the overall breath test result and the overall scintigraphy test result are normal, wherein said stomach abnormal classification is used when both the overall breath test result and the overall scintigraphy test result are abnormal, and wherein said post-stomach abnormal classification is used when the overall breath test result is abnormal and the overall scintigraphy test result is normal.

13. The method of claim 12, wherein said periodic time points include 45, 90, 120, 150, 180 and/or 240 minute time points.

14. The method of claim 12, wherein said scintigraphic test result at each of said periodic time points is expressed as % Prop.

15. The method of claim 12, wherein said breath test result at each of said periodic time points is expressed as kPCD.

16. The method of claim 12, wherein the obtaining a scintigraphic test result and a breath test result for each of said periodic time points comprises:
  classifying the scintigraphic test result as normal or abnormal, said scintigraphic test result being classified as normal when falling within a scintigraphic reference range that reflects a range of test results for normal patients and being classified as abnormal when falling outside of said scintigraphic reference range; and
  classifying the breath test result as normal or abnormal, said breath test result being classified as normal when falling within a breath test reference range that reflects a range of test results for normal patients and being classified as abnormal when falling outside of said breath test reference range.

17. The method of claim 16, wherein each of said scintigraphic reference range and said breath test reference range has an upper cutoff point and a lower cutoff point, the upper cutoff point demarcating normal gastric emptying from rapid gastric emptying and the lower cutoff point demarcating normal gastric emptying from slow gastric emptying.

18. The method of claim 12, wherein the providing an overall scintigraphic test result comprises evaluating the scintigraphic test result at a selected time point and the providing an overall breath test result comprises evaluating the breath test result at said selected time point.

19. The method of claim 18 wherein the overall scintigraphic test result is classified as abnormal if the scintigraphic test result at the selected time point is abnormal and wherein the overall breath test result is classified as abnormal if the breath test result at the selected time point is abnormal.

20. The method of claim 18 wherein the selected time point is a 90 minute time point.

21. The method of claim 18 wherein the selected time point is a 120 minute time point.

22. The method of claim 12, wherein said breath test label is incorporated into a biomass composed of cells including proteins, carbohydrates, and lipids.

23. The method of claim 12, wherein said biomass is *Spirulina platensis*.

24. The method of claim 12, wherein said breath test label is $^{13}C$.

* * * * *